United States Patent
Grant

(10) Patent No.: US 6,578,965 B2
(45) Date of Patent: Jun. 17, 2003

(54) OBJECTIVE SYSTEM AND METHOD FOR EVALUATING OCULAR CHANGES INCLUDING ASSESSMENT OF MACULAR INTEGRITY AND FUNCTION

(76) Inventor: Alan H. Grant, 3208 Woodhollow Dr., Chevy Chase, MD (US) 20815

( * ) Notice: Subject to any disclaimer, the term of this patent is extended or adjusted under 35 U.S.C. 154(b) by 0 days.

(21) Appl. No.: 09/895,067

(22) Filed: Jul. 2, 2001

(65) Prior Publication Data

US 2003/0002014 A1 Jan. 2, 2003

(51) Int. Cl.[7] ............................. A61B 3/10; A61B 13/00
(52) U.S. Cl. ..................... 351/214; 351/211; 351/221; 600/558
(58) Field of Search ...................... 351/200, 202, 351/205, 209, 214, 221, 222, 239, 243, 246; 600/558

(56) References Cited

U.S. PATENT DOCUMENTS

| | | |
|---|---|---|
| 3,000,271 A | 9/1961 | Harvey et al. |
| 3,450,466 A | 6/1969 | Streisinger |
| 3,542,457 A | 11/1970 | Balding |
| 3,883,235 A | 5/1975 | Lynn et al. |
| 4,586,796 A | 5/1986 | Molteno |
| 5,002,385 A * | 3/1991 | Kasahara et al. ........... 351/209 |
| 5,293,535 A | 3/1994 | Sensui |
| 5,502,520 A | 3/1996 | Cibis et al. |
| 5,838,422 A | 11/1998 | Caskey |
| 5,908,394 A | 6/1999 | Kandel et al. |
| 5,942,954 A * | 8/1999 | Galiana et al. ............. 351/209 |
| 5,943,116 A | 8/1999 | Zeimer |
| 5,946,075 A * | 8/1999 | Horn .......................... 351/237 |
| 5,989,194 A | 11/1999 | Davenport et al. |
| 6,002,484 A | 12/1999 | Rozema et al. |
| 6,089,716 A | 7/2000 | Lashkari et al. |
| 6,315,412 B1 * | 11/2001 | Snodderly et al. .......... 351/200 |

* cited by examiner

*Primary Examiner*—Marvin M. Lateef
*Assistant Examiner*—John R. Sanders
(74) *Attorney, Agent, or Firm*—Jacobson Holman PLLC

(57) ABSTRACT

A system and method for objectively testing for ocular changes including age-related macular degeneration through reliance on involuntary physical reactions such as the fixation reflex and optokinetic nystagmus. A narrow band of visible blue light is beamed at the patient's eye through alternate apertures in a mask which are separated by a relatively small angle of subtendance at the entrance pupil. In the presence of a healthy macula, the blue light is filtered out and the fixation reflex is absent. Conversely, if the macula is in the process of degenerating by the progressive loss of protective pigments, then the impinging of the narrow band of visible blue light upon the macula, via the alternate apertures, will evoke the fixation reflex.

32 Claims, 1 Drawing Sheet

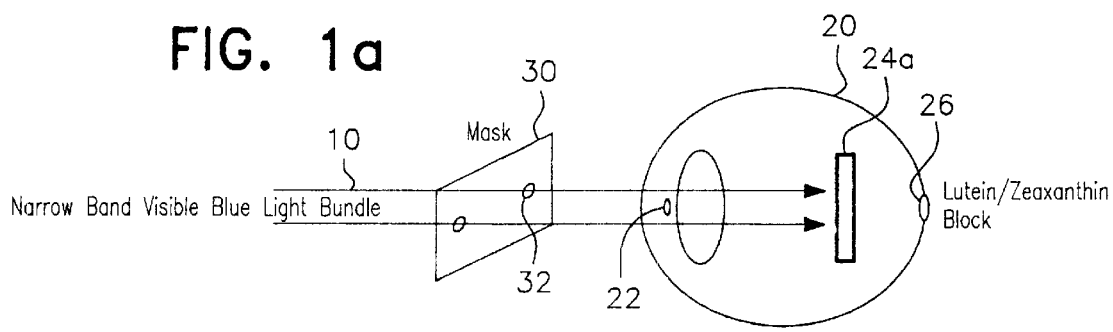
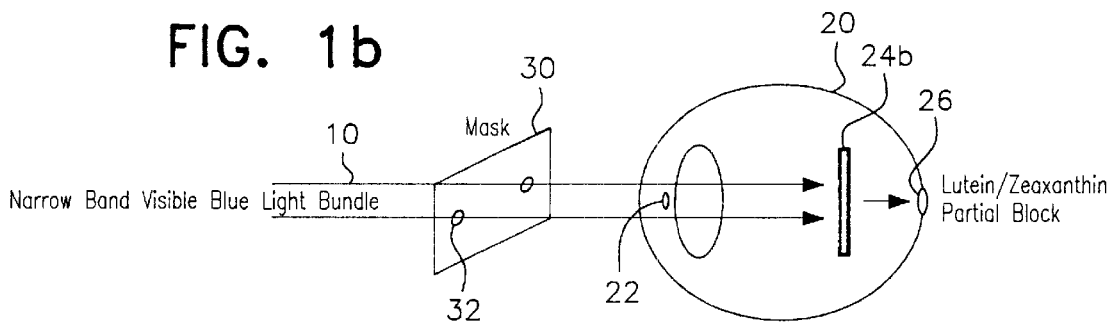
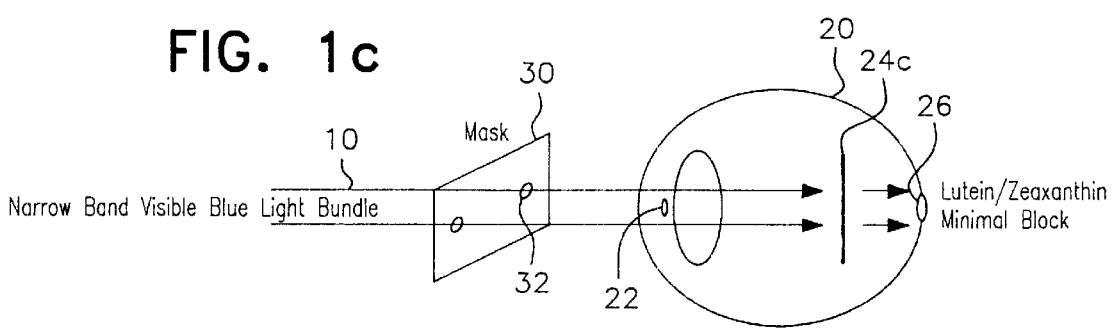
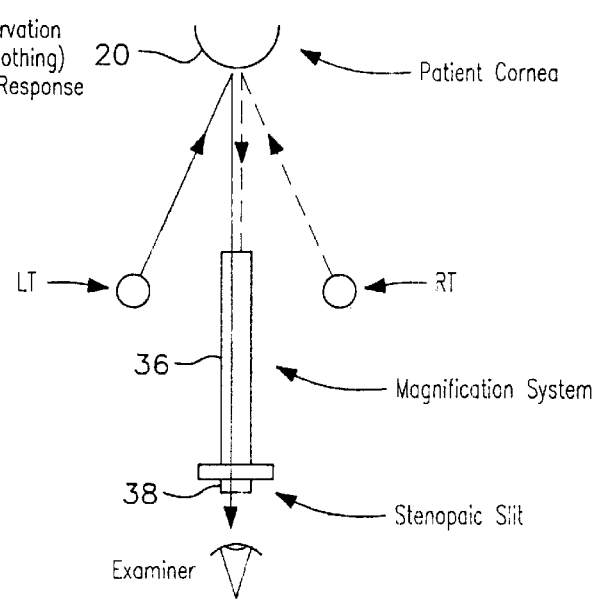

OBJECTIVE SYSTEM AND METHOD FOR EVALUATING OCULAR CHANGES INCLUDING ASSESSMENT OF MACULAR INTEGRITY AND FUNCTION

BACKGROUND OF THE INVENTION

1. Field of the Invention

The present invention is related to the field of ocular health, disease and degeneration and, more particularly, to a noninvasive system and objective method for analyzing macular function and thereby detecting macular changes and degradations, which may be predictive of future age-related macular degeneration.

2. Description of the Related Art

Human longevity is extending, and we are increasingly subject to adverse physiological changes which are detrimental to our well-being and independence. Loss of visual acuity, which may or may not lead ultimately to blindness, can be debilitating. The macula lutea, a small area lying slightly lateral to the center of the retina, represents the region of maximum visual acuity in the human eye. While many age-related ocular changes such as cataract formation, adult-onset diabetes, and glaucoma can be reasonably well-managed so that visual self-sufficiency can be maintained, Age-related Macular Degeneration (AMD) impacting the macula lutea is progressively the most debilitating exception.

Evaluation of the macula lutea has traditionally been limited to subjective testing. By definition, subjective testing is flawed and individually anecdotal, due to total reliance on patient responses.

The earliest subjective test for patient awareness of macular changes is a graphed target known as the Amsler Grid, which requires visualization, mental evaluation, verbalized response, and remembrance for comparison with the same test conducted at an earlier time. This is inherently unreliable. There are many other subjective tests, including contrast sensitivity testing, kinetic and static perimetry, subjective manifest refraction, and color discrimination testing, but these are also anecdotal because of reliance on articulated responses, and therefore incorporate whatever subjective bias may be present. In addition, the subjectivity of any type of testing is compounded by the subjective interpreted experience/bias of the test proctor.

By the time an ophthalmoscopic examination reveals observable changes in the macula, the disease process is well established. Similarly, by the time the patient notices significant loss of visual acuity, that is uncorrectible, and/or distortion of the Amsler Grid, the disease process is well established. Current therapies include Photo-Dynamic Therapy and Macular Translocation which are medical interventions principally used when the AMD disease process has been well established and there are serious decrements in visual acuity.

It is estimated that AMD affects 20% of the population over age 65 and 37% of the population over age 75. The inference must be that the tendency toward AMD exists at an undiagnosed pre-clinical level at much earlier ages.

There is, therefore, a need for objective assessment of macular function, starting early in life, to identify any pre-disposition to develop AMD. This would then stimulate the search for constructive prophylactic strategies to forestall the future onset/progression of the disease.

SUMMARY OF THE INVENTION

In view of the foregoing, one object of the present invention is to provide an objective system and method for assessing macular function.

Another object of the invention is a system and method for objectively assessing macular function on an ongoing basis, beginning early in life, so as to detect any type of macular and other possible ocular changes, including AMD in preliminary stages, and determine risk factors associated with AMD for AMD prediction.

A further object of the invention is a system and method using selective light-wave stimulation to induce physiologic responses that indicate that macular or other possible ocular changes are occurring.

A still further object of the invention is a system and method for objectively determining AMD using visible blue light to induce a fixation reflex and/or optokinetic nystagmus.

In accordance with this and other objects, the present invention is directed to a system and method for objectively and non-invasively testing for macular and/or other ocular changes. According to the method, a narrow band of blue light within the visible light spectrum is alternately beamed at a patient's eye through two distinct apertures in a mask which are separated by a relatively small angle of subtendance at the entrance pupil. In the event of a healthy macula, the blue light is filtered out and the patient will not exhibit a fixation reflex. If the macula is in the process of degenerating, however, the impinging of the narrow band of blue light upon the macula, via the alternate apertures, should evoke the fixation reflex. Because the fixation reflex is involuntary, the method of the present invention allows macular health to be objectively determined.

The system includes a plurality of targets separated from one another by a distance, each target emanating a specified wavelength of visible blue light. The plurality of targets are illuminated sequentially or alternately such that only one target is fully illuminated at any given point in time. An examiner observes the eye of the patient using a magnification system with a stenopaic slit for narrowing a lateral field of view of a vertical-line image to be perceived by the examiner. As the targets are sequentially illuminated, an involuntary reaction will be induced to some degree in the patient's eye, if such individual has undergone some macular changes (which may later lead to macular degeneration.

These and other objects of the invention, as well as many of the intended advantages thereof, will become more readily apparent when reference is made to the following description taken in conjunction with the accompanying drawings.

BRIEF DESCRIPTION OF THE DRAWINGS

FIGS. 1a–1c illustrate varying function of the macula as detected according to the present invention; and FIG. 2 shows an arrangement of testing equipment in accordance with the system of the present invention.

DETAILED DESCRIPTION OF THE PREFERRED EMBODIMENTS

Although only one preferred embodiment of the invention is explained in detail, it is to be understood that the embodiment is given by way of illustration only. It is not intended that the invention be limited in its scope to the specific details of construction and methodology set forth in the following description or illustrated in the drawings. Also, in describing the preferred embodiments, specific terminology will be resorted to for the sake of clarity. It is to be understood that each specific term includes all technical equivalents which operate in a similar manner to accomplish a similar purpose.

The macula lutea represents the region of maximum visual acuity in the human eye. The yellowish color of the macula lutea, which is generally referred to herein as "the macula", contains protective elements in the retina such as lutein and zeaxanthin. These elements are lipid-soluble xanthophyll carotenoids (singlet oxygen quenchers) which enter the eye from plasma and accumulate in the retina, acting as strong antioxidants which neutralize free radicals that can and do damage individual cells. Their function is to filter out visible blue light.

With the passage of time within a human life-cycle, there are many influences which alter the early-in-life pristine functionality of the macula. There is normally an irregular dip in the blue end of the visible spectrum (440–490 nm), and there is a gradual and selective loss of sensitivity to blue light by the short visible wavelength-sensitive blue cones. AMD is thought to develop because, whereas the cornea and the crystalline lens are known to filter out ultra-violet light, unabsorbed visible blue light passes through these structures and reaches the retinal surface, impinges on the macula and, over time, can cause photodamage that contributes to macular degeneration.

There is some evidence that dietary ingestion of lutein and zeaxanthin, which are found in dark green leafy vegetables such as spinach, kale, and collard greens, and/or in supplements, may decrease somewhat the risk, onset, or progression of AMD. Researchers at Harvard Medical School have noted significantly lower AMD risk (43%) in subjects with high intake of lutein and zeaxanthin carotenoids. In one test, where 30 mg per day of lutein were taken for a period of 140 days, the macular pigment density increased, corresponding to a 30–40% reduction in the amount of blue light that would reach the blue cone photoreceptors. It also appears that subjects of the same age who have higher macular pigment density, have greater visual sensitivity similar to that of younger subjects.

Differential retinal functionality factors suggest practicality of selective narrow band stimulation/non-stimulation of the blue cone photoreceptors in the macula to develop an objective assessment method. These factors include cone population (foveola contains approximately 30,000 cones, as compared to approximately 130 million receptors in the entire retinal surface; any focal test stimulus will also evoke a response from adjacent receptors, indicating that foveal/macular ERG cannot be totally isolated); wavelength discrimination (as little as a 1 nm difference may be discriminated in the region of 490 nm to 585 nm; at the short and long ends of the visible spectrum, the sensitivity decreases to 4 nm); spectral sensitivity (the blue cone photoreceptors peak at approximately 440 nm to 450 nm); Stiles-Crawford effect (light entering the center of the pupil has greater registry on the densely packed foveomacular cones because it strikes these receptors axially and not obliquely); early receptor potential (ERP) (cones dominate the ERP despite rhodopsin being the dominant visual pigment, because cone-disc lumina abut the extra-cellular space or vitreous, while rod discs are separated by a plasma membrane from the vitreous); and blue filter puzzle (reading comprehension in the presence of blue filters demonstrates significant improvement for reading-disabled children versus normal-reading children; why selective spectral transmission is salutary for one group in this study is presently unknown).

Age-related macular degeneration has a relationship to the fixation reflex and to optokinetic nystagmus. Both of these phenomenon are macular-foveal, involuntary reflexes and are precipitated by movement of an object or objects in the visual field. The eyes respond by jumping back and forth with successive saccads, or re-fixations, on each new target which is presented. These reflexes have an evolutionary basis, being unconditionally reflexive as a product of brainstem activity.

The present invention makes use of both the human involuntary reflexes and the relationship between macular degeneration and visible blue light to provide a system and method for objective AMD testing. As illustrated in FIGS. 1a through 1c, the system includes a mechanism whereby a narrow band of visible blue light 10 is alternately beamed at the subject's eye 20 through alternate apertures 32, either lines or spots, in a mask 30, the apertures 32 being separated by a relatively small angle of subtendance at the entrance pupil 22. In a preferred embodiment, the angle of subtendance may range from as little as 5–6 degrees to as much as 30–40 degrees.

If the macula 26 is totally healthy with no diminution of the lutein/zeaxanthin block 24a, as represented in FIG. 1a, then the subject will not see the blue light and the fixation reflex will be absent. If, however, the macula 26 is in the process of degenerating due to the progressive loss of yellow pigments, then the impinging of the narrow band of visible blue light upon the macula 26, via the alternate apertures, should evoke the fixation reflex. FIG. 1b illustrates a partial lutein/zeaxanthin block 24b allowing blue light to damage the macula, while FIG. 1c depicts a minimal lutein/zeaxanthin block 24c resulting in greater macular deterioration.

Observing the time of onset, as well as the intensity, of the fixation reflex then provides an index of the health of the macula or its rate of degeneration.

An alternative method is to present to the patient, using the same narrow band of blue visible light, a parade of successive spots or lines across the visual field. If the macula has begun to deteriorate, the presentation of successive lights will evoke an involuntary optokinetic nystagmus response. Whether reliance is made upon the fixation reflex or the optokinetic nystagmus response, because the outcome of these testing techniques depends upon an involuntary reaction, the testing procedures according to the present invention are free of subjectivity.

Since horizontal/lateral saccads constitute the dominant manner of fixation reflex, this testing mechanism applies to virtually all variations in upper and lower lid positioning between reflex blinks, i.e., the vertical aperture size. An exception would be in the presence of a marked ptosis, wherein the upper lid completely covers the pupil. Testing of this subject would require mechanically elevating and restraining the upper lid to uncover the pupil.

To produce the narrow band of blue light, a narrow bandpass filter may be used to obtain a spike of high transmittance (approximately 60%) of light within a very limited nanometer range, e.g., 30–40 nm, which can effectively cut off virtually all light transmission above a desired nanometer range. This "spike" transmission filter may also be coupled with an edge filter which will only transmit light below a certain wavelength (approximately 450 nm). Examples of filters that may be used include:

Corion Corporation
  Bandpass filter: P70–400; 400 nm; transmittance 60%; bandwidth 70 nm
  Edge filter: LS-450; cutoff 450 nm; transmittance 65%
Schott—Visible Bandpass Filters
  BG-12; peak transmittance 402 nm, 82%; bandwidth 200 nm Kodak Wratten Gelatin Filters 47B: 430 nm, 50% transmittance; bandwidth 140 nm 98: 435 nm, 50% transmittance; bandwidth 120 nm Other testing variables include target width, shape (slits or slots) and/or diameter; angular distance between two fixation reflex targets; angular distance between successive optokinetic nystagmus targets; time interval between presentation of each target; wavelength alterations—tunable narrowband spikes; light intensities (rheostat control of intensity of target illumination) and contrast thresholds; and light adaptation versus dark adaptation.

With regard to wavelength alterations, it may be that if the narrowband spike can be sufficiently thinned, e.g., to less than 10 nm, and beamed at the foveola centralis, then the wavelength may be of any approximate value within the visible spectrum of approximately 360 to 720 nm. Atomic spectrometry can scan incoming light of any wavelength from 350–600 nm, i.e., 361 nm resolution at full-width/half height@0.22 nm. Wavelengths in the ultraviolet and/or infrared spectrum may also be used in some instances, depending upon the ocular condition being evaluated.

Contrast threshold needs to be adjusted to determine the relationship between illumination of two adjacent areas in order to determine what brightness is needed to stimulate the foveo/macular cones.

Light versus dark adaption ranges between a fully light-adapted subject and a fully dark-adapted subject. The fully light-adapted subject is tested immediately after environmental light is removed. In a fully dark-adapted subject, scotopic sensitivity shift to shorter wavelength (from approximately 560 nm to 510 nm) may further enhance the filtering-out effect of longer wavelengths.

For variations in the testing procedure, the left target and the right target may have an adjustable separation distance capability. In addition, with rheostat control, variations in emerging light intensities are possible, whether of one or both targets. Furthermore, it may be desirable to have, as an example, the left target gradually diminish in intensity while the right target turns on, as opposed to having the left target turn off completely in a single instant.

A system for conducting the testing procedure in accordance with the present invention is illustrated in FIG. 2. As shown, a left target LT and a right target RT are presented to the eye 20 of the subject and alternatively lighted. In a preferred embodiment, each target is faced with a filter, or combination of filters, which totally block out virtually all wavelengths of light emanating from the lighted targets LT, RT that are longer than 400 nm and shorter than 350 nm.

During practice of the invention, the patient needs no verbal instructions. Each eye is tested separately. The testing environment is darkened and the only illumination first emanates from LT. The examiner observes the patient's eye through a magnification system 36. When LT is either completely shut off in favor of RT being turned on, or if LT simply diminishes in intensity to 60–70% from its initial lighted value at the same instant that RT turn on to its maximum intensity, the result is the potential for the eye to have an involuntary fixation shift from LT to RT. A septum baffle (not shown) between LT and RT prevents any light from crossing over to illuminate the opposite side. Alternately RT is turned on when LT turns off and vice versa. The sequence is repeated multiple times while the examiner continues to observe the presence or absence of saccads.

In observing and quantifying the fixation reflex, use is made of Purkinje images. As is known in the art, there are four of these images, the first from the front corneal surface, which is the brightest, the second coming from the rear corneal surface, the third coming from the front lenticular surface, and the fourth coming from the rear lenticular surface. Purkinje image techniques, including the Double Purkinje image technique which relies upon alignment of two Purkinje images, are known in the art.

Because unaided observation of the onset of the fixation reflex is gross and insufficient, ocular observance of the presence or absence of the fixation reflex may be accomplished by placing a vertically oriented stenopaic slit 38 in front of the examiner's eyepiece. This slit narrows the lateral field of view of the perceived vertical-line image, derived from the 1st Purkinje image. A first testing sequence is performed in which LT is initially illuminated and then LT is turned off, simultaneously with RT turning on. If no fixation reflex is induced, i.e., there is no shift of the patient's eye from LT to RT, then the vertical-line image disappears from the view of the examiner. If a fixation reflex is induced, i.e., the patient's eye shifts from LT to RT, then the examiner will continue to see a vertical-line image.

Various angle metrology methods may be undertaken to note and quantify the involuntary response. For example, a half-silvered haploscopic mirror may be interposed between the patient's eye and the LT and RT. This mirror will convey any reflected 1st Purkinje image light coming back from the eye being tested to laterally placed photocell detectors such as a motion-detecting diode. Alternative oculography includes recording the shift in position of reflected/scattered light from the sclero-limbal junction or from the iris/pupil junction. According to a preferred embodiment, the Double Purkinje image technique may also be used, namely, when the right eye is fixated upon LT, the 1st and 4th Purkinje images are aligned. Upon fixation shift, an induced parallax demonstrates these two images to be separated from one another (referred to as angle kappa). This technique is quite sensitive and can discriminate as little as one minute of arc of ocular position change, within one millisecond.

Ocular observation demonstrates whether the fixation reflex has been an all-or-nothing response. Angle metrology demonstrates degrees of graduated responses, which may be dependent upon other variables. Some possible variables, which may work separately or in combination to affect response, include travel speed from one target to another, relative light intensities of the targets, distance between the targets, the time interval between illumination of the each target, and the number of target cycles. Other variables may also need to be considered.

Using the present invention, it will be possible to obtain both latitudinal (many testee subjects within a given age grouping), and longitudinal (retesting of the same individuals at different ages) data to determine the significance of changes in the characteristics of the fixation reflex.

In summary, the sophisticated remediation techniques mentioned at the outset, e.g., Photodynamic Therapy and Macular Translocation, are admirable in trying to stabilize neovascular AMD and to possible restore some portion of the diminished visual efficiency. But by the time these measures are initiated, the early-in-life potential prophylaxis has been lost. Therefore, it is important to gain a better understanding of macular function in large numbers of juveniles, teenagers and young adults. This suggests that the development of a reliably precise objective testing procedure such as the present invention, which can be used both latitudinally and longitudinally to accumulate a large base of testee data, would be of great benefit.

The foregoing descriptions and drawings should be considered as illustrative only of the principles of the invention.

The invention may be configured in other ways and is not limited to the particular configuration of the preferred embodiment. Numerous applications of the present invention will readily occur to those skilled in the art. For example, it will be apparent to one of skill in the art that the present invention may further be used to test individual response to other wavelengths of light for other purposes and to measure other functions, apart from macular health. Any wavelength within the visible light spectrum, or even in the infrared or ultraviolet ranges, may be of use for particular testing purposes. Therefore, it is not desired to limit the invention to the specific examples disclosed or the exact construction and operation shown and described. Rather, all suitable modifications and equivalents may be resorted to, falling within the scope of the invention.

What is claimed is:

1. A method for evaluating ocular function in a patient comprising the steps of:
    a) illuminating a first target and directing a first specific wavelength of light in a range of 300 to 450 nm toward an eye of the patient from said first target;
    b) reducing a luminance of said first target while substantially simultaneously illuminating a second target located at a distance from said first target and directing a second specific wavelength of light toward the eye of the patient; and
    c) observing the eye of the patient by an examiner to detect an involuntary reflex response of the eye to the previous steps.

2. The method as set forth in claim 1, further comprising after step b) the steps of:
    b1) reducing a luminance of said second target while substantially simultaneously illuminating the first target and redirecting the first specific wavelength of light toward the eye of the patient;
    b2) repeating steps b) and b1) sequentially, while performing step c).

3. The method as set forth in claim 1, wherein the involuntary reflex response is optokinetic nystagmus.

4. The method as set forth in claim 1, wherein the first and second wavelengths are substantially the same.

5. The method as set forth in claim 1, further comprising before step a) the step of interposing a half-silvered haploscopic mirror between the patient's eye and the first and second targets.

6. The method as set forth in claim 1, wherein the second wavelength is in a range between 300 nm and 450 nm.

7. A method for evaluating ocular changes in a patient comprising the steps of:
    a) illuminating a first target and directing only a first specific wavelength of visible blue light toward an eye of the patient from said first target, other wavelengths being blocked by a filter over said first target;
    b) reducing a luminance of said first target while substantially simultaneously illuminating a second target located at a distance from said first target and directing only a second specific wavelength of visible blue light toward the eye of the patient, other wavelengths being blocked by a filter over said second target;
    c) observing the eye of the patient by an examiner to detect an involuntary reflex response of the eye to the previous steps.

8. The method as set forth in claim 7, further comprising after step b) the steps of:
    b1) reducing a luminance of said second target while substantially simultaneously illuminating the first target and redirecting the first specific wavelength of visible blue light toward the eye of the patient;
    b2) repeating steps b) and b1) sequentially, while performing step c).

9. The method as set forth in claim 7, wherein the involuntary reflex response is a fixation reflex.

10. The method as set forth in claim 9, wherein step c) comprises the steps of:
    placing a stenopaic slit in front of an eye of the examiner, narrowing a lateral field of view of a perceived vertical-line image;
    viewing, by said examiner, said vertical-line image in response to inducement of the fixation reflex in the patient;
    viewing, by said examiner, an absence of said vertical-line image in response to an absence of the fixation reflex in the patient.

11. The method as set forth in claim 10, wherein each of the first and the second wavelengths is in a range between 300 nm and 450 nm.

12. The method as set forth in claim 7, wherein the involuntary reflex response is optokinetic nystagmus.

13. The method as set forth in claim 7, wherein the first and second wavelengths of visible blue light are substantially the same, and the step of reducing turns off the first target.

14. The method as set forth in claim 7, further comprising before step a) the step of interposing a half-silvered haploscopic mirror between the patient's eye and the first and second targets.

15. The method as set forth in claim 7, wherein the first wavelength is in a range between 300 nm and 450 nm.

16. The method as set forth in claim 15, wherein the second wavelength is in a range between 300 nm and 450 nm.

17. A method for evaluating ocular changes in a patient comprising the steps of:
    a) emanating from a first target only a first specific wavelength of light toward an eye of the patient;
    b) reducing a luminance of said first target while substantially simultaneously emanating from a second target located at a distance from said first target only a second specific wavelength of light toward the eye of the patient; and
    c) observing the eye of the patient by an examiner to detect an involuntary reflex response of the eye to the previous steps, wherein the first and second wavelengths being within a visible light spectrum of approximately 360–720 nm.

18. The method as set forth in claim 17, further comprising after step b) the steps of:
    b1) reducing a luminance of said second target while substantially simultaneously emanating the first specific wavelength of light from the first target toward the eye of the patient;
    b2) repeating steps b) and b1) sequentially, while performing step c).

19. The method as set forth in claim 17, wherein the involuntary reflex response is one of a fixation reflex and optokinetic nystagmus.

20. The method as set forth in claim 17, wherein the first and second wavelengths are substantially the same and fall within a range of visible blue light.

21. The method as set forth in claim 17, further comprising before step a) the step of interposing a half-silvered haploscopic mirror between the patient's eye and the first and second targets.

22. A system for evaluating ocular changes in an eye of a patient, comprising:
- a plurality of targets separated from one another by a distance, each target emanating a specified wavelength of visible blue light toward the eye of the patient, said plurality of targets being illuminated sequentially such that only one target is fully illuminated at any given point in time;
- a magnification system for observing the patient's eye by an examiner; and
- a stenopaic slit located on an end of said magnification system nearest the examiner for narrowing a lateral field of view of a vertical-line image perceived by said examiner;
- wherein the sequential illumination of said plurality of targets induces an involuntary reaction in the eye of said patient which is detectable by said examiner when said patient has at least some macular degradation and/or macular degeneration.

23. The method as set forth in claim 22, wherein the involuntary reflex response is a fixation reflex.

24. The system as set forth in claim 23, said plurality of targets including a left target and a right target, relative to said patient, said magnification system situated between said left and right targets.

25. The system as set forth in claim 24, wherein during operation of said system, the left target is illuminated while the right target is turned off and alternately when the right target is illuminated, the left target is turned off, said examiner continuing to perceive said vertical line image through said stenopaic slit when a fixation reflex is induced in said patient.

26. The system as set forth in claim 23, said plurality of targets created by alternate apertures in a mask, said apertures being separated by a small angle of subtendance.

27. The system as set forth in claim 26, wherein the angle of subtendance is in a range from 5 to 40 degrees.

28. The method as set forth in claim 22, wherein the involuntary reflex response is optokinetic nystagmus.

29. The system as set forth in claim 28, said plurality of targets including a sequence of targets extending across the patient's field of view, said sequence of targets being illuminated in series from left to right or from right to left relative to said patient.

30. The system as set forth in claim 22, further comprising a filter associated with said plurality of targets for blocking out all wavelengths other than said specified wavelength.

31. A method for evaluating ocular function in a patient comprising the steps of:
- a) illuminating a first target and directing a first specific wavelength of light toward an eye of the patient from said first target;
- b) reducing a luminance of said first target while substantially simultaneously illuminating a second target located at a distance from said first target and directing a second specific wavelength of light toward the eye of the patient; and
- c) observing the eye of the patient by an examiner to detect a fixation reflex response of the eye to the previous steps by:
  - placing a stenopaic slit in front of an eye of the examiner, narrowing a lateral field of view of a perceived vertical-line image;
  - viewing, by said examiner, said vertical-line image in response to inducement of the fixation reflex in the patient; and
  - viewing, by said examiner, an absence of said vertical-line image in response to an absence of the fixation reflex in the patient.

32. A method for evaluating ocular changes in a patient comprising the steps of:
- a) emanating from a first target only a first specific wavelength of light toward an eye of the patient;
- b) reducing a luminance of said first target while substantially simultaneously emanating from a second target located at a distance from said first target only a second specific wavelength of light toward the eye of the patient;
- c) observing the eye of the patient by an examiner to detect an involuntary reflex response of the eye to the previous steps by:
  - placing a stenopaic slit in front of an eye of the examiner, narrowing a lateral field of view of a perceived vertical line image;
  - viewing, by said examiner, said vertical-line image in response to inducement of the involuntary reflex response in the patient; and
  - viewing, by said examiner, an absence of said vertical-line image in response to an absence of said involuntary reflex response in the patient.

* * * * *